US009921489B2

(12) United States Patent
Singh et al.

(10) Patent No.: US 9,921,489 B2
(45) Date of Patent: Mar. 20, 2018

(54) FOCUS MONITORING ARRANGEMENT AND INSPECTION APPARATUS INCLUDING SUCH AN ARRANGEMENT

(71) Applicant: ASML Netherlands B.V., Veldhoven (NL)

(72) Inventors: Amandev Singh, Eindhoven (NL); Henricus Petrus Maria Pellemans, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 14 days.

(21) Appl. No.: 14/867,594

(22) Filed: Sep. 28, 2015

(65) Prior Publication Data

US 2016/0097984 A1 Apr. 7, 2016

(30) Foreign Application Priority Data

Oct. 3, 2014 (EP) .................................... 14187646

(51) Int. Cl.
G01B 9/00 (2006.01)
G03F 7/20 (2006.01)
(Continued)

(52) U.S. Cl.
CPC ...... G03F 7/70641 (2013.01); G03F 7/70616 (2013.01); G03F 9/7026 (2013.01); G02B 21/245 (2013.01)

(58) Field of Classification Search
CPC ......... G01M 11/0228; G01M 11/0221; G01M 11/0264; G01M 11/0285; A61B 3/103
(Continued)

(56) References Cited

U.S. PATENT DOCUMENTS 7,193,231 B2 3/2007 Lof et al.
7,630,070 B2 12/2009 Hugers
(Continued)

FOREIGN PATENT DOCUMENTS

CN 103308149 A 9/2013
DE 10 2010 016862 A1 11/2011
(Continued)

OTHER PUBLICATIONS

International Search Report directed to App. No. PCT/EP2015/070410, dated Nov. 16, 2015; 3 pages.
(Continued)

*Primary Examiner* — Tarifur Chowdhury
*Assistant Examiner* — Md M Rahman
(74) *Attorney, Agent, or Firm* — Sterne, Kessler, Goldstein & Fox P.L.L.C.

(57) ABSTRACT

An inspection apparatus (300) includes a focus monitoring arrangement (500, 500'). Focusing radiation (505) comprises radiation having a first wavelength and radiation having a second wavelength. Reference radiation and focusing radiation at each wavelength are provided with at least one relative frequency shift so that the interfering radiation detected in the detection system includes a time-varying component having a characteristic frequency. A focus detection system (520) comprises one or more lock-in detectors (520b, 520c, 900). Operating the lock-in detectors with reference to both the first and second characteristic frequencies allows the arrangement to select which of the first and second focusing radiation is used to determine whether the optical system is in focus. Good quality signals can be obtained from targets of different structure.

23 Claims, 7 Drawing Sheets

(51) Int. Cl.
*G03F 9/00* (2006.01)
*G02B 21/24* (2006.01)

(58) Field of Classification Search
USPC .......................................................... 356/126
See application file for complete search history.

(56) References Cited

U.S. PATENT DOCUMENTS

| | | |
|---|---|---|
| 7,791,732 B2 | 9/2010 | Den Boef et al. |
| 7,869,022 B2 | 1/2011 | Van Boxmeer et al. |
| 8,125,615 B2 | 2/2012 | Kalf et al. |
| 8,982,339 B2 | 3/2015 | Schönleber et al. |
| 8,994,921 B2 | 3/2015 | Van Boxmeer et al. |
| 2004/0042014 A1* | 3/2004 | Feldman ............ G01N 21/8851 356/484 |
| 2006/0033921 A1 | 2/2006 | Den Boef et al. |
| 2006/0066855 A1 | 3/2006 | Boef et al. |
| 2008/0151228 A1 | 6/2008 | Hugers |
| 2010/0155375 A1 | 6/2010 | Dietz et al. |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0013913 A1* | 1/2012 | Ignatovich ......... G01B 9/02007 356/479 |
| 2012/0044470 A1 | 2/2012 | Smilde et al. |
| 2012/0123581 A1 | 5/2012 | Smilde et al. |
| 2013/0183833 A1* | 7/2013 | Duan ................. B23K 26/0613 438/778 |
| 2013/0258310 A1 | 10/2013 | Smilde et al. |
| 2013/0271740 A1 | 10/2013 | Quintanilha |
| 2014/0139814 A1 | 5/2014 | Cramer et al. |
| 2014/0183362 A1* | 7/2014 | Islam ...................... G01J 3/453 250/338.4 |
| 2015/0261097 A1 | 1/2015 | Mathijssen et al. |

FOREIGN PATENT DOCUMENTS

| | | |
|---|---|---|
| JP | S59 79104 A | 5/1984 |
| WO | WO 2012/126718 A1 | 9/2012 |
| WO | WO 2013/178422 A1 | 12/2013 |
| WO | WO 2014/082938 A1 | 6/2014 |

OTHER PUBLICATIONS

English-Language Translation of App. Pub. No. CN 103308149 A, published Sep. 18, 2013; 7 pages.
English-Language Abstract of App. Pub. No. JP S59-79104 A, published May 8, 1984; 1 page.

* cited by examiner

FOCUS MONITORING ARRANGEMENT AND INSPECTION APPARATUS INCLUDING SUCH AN ARRANGEMENT

FIELD

The present invention relates to focus monitoring arrangements for optical systems. The invention may be applied or example in inspection apparatus and lithographic apparatuses usable, for example, in the manufacture of devices by lithographic techniques.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 20120126718. Methods and scatterometers are also disclosed in US20110027704A1, US2006033921A1 and US2010201963A1. The targets used by such scatterometers are relatively large, e.g., 40 µm by 40 µm, gratings and the measurement beam generates an illumination spot that is smaller than the grating (i.e., the grating is underfilled). In addition to scatterometry to determine parameters of a structure made in one patterning step, the methods and apparatus can be applied to perform diffraction-based overlay measurements.

Diffraction-based overlay metrology using dark-field image detection of the diffraction orders enables overlay measurements on smaller targets. These targets can be smaller than the illumination spot and may be surrounded by product structures on a wafer. Multiple targets can be measured in one image. Examples of dark-field imaging metrology can be found in international patent applications US2010328655 A1 and US2011069292 A1 which documents are hereby incorporated by reference in their entirety. Further developments of the technique have been described in published patent publications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference. The invention is not limited in application to any particular type of inspection apparatus, or even to inspection apparatuses generally.

A common problem in inspection apparatuses and other optical systems is one of controlling focusing of the optical system onto a target. Whether the optical system is for inspection by imaging, by scatterometry or for other purposes such as treatment of surfaces, many systems require real-time control of focus of the optical system, within very tight tolerances. A focus control arrangement for a scatterometer of the type described above is disclosed for example in published patent application US20080151228A. Light reflected from the target is imaged with deliberate focus error on two photodetectors. Comparing the illuminated area between the two photodetectors allows an indication of defocus to be obtained, and the direction of defocus to be identified. The contents of that application are incorporated herein by reference.

Current instruments using the known arrangement can achieve focus accuracy within around ±200 nanometers. However, the known arrangement also suffers from limitations in use.) It is also necessary for the focusing light to share the optical system with other radiations that relate to the main function of the optical system. A single wavelength with limited power is therefore used for focusing. Unfortunately, in an inspection application designed to test a variety of targets, it cannot be guaranteed that all target types will reflect the single wavelength with a good signal strength. (In other words, some types of target will be easier to focus on than others. It is therefore difficult in practice to obtain focusing signals with a good dynamic range (rejection of noise) in all situations.

SUMMARY

The inventors have recognized that improved dynamic range and noise rejection can be obtained by applying an interferometric technique and lock-in detection in a focus control arrangement. Alternatively or in addition, use of lock-in detection allows different wavelengths of radiation to be used for focus monitoring, allowing good quality control over a wider range of targets.

The invention in a first aspect provides a focus monitoring arrangement for an optical system, comprising:
- a focusing beam delivery system for delivering to said optical system focusing radiation, the optical system being arranged to deliver the focusing radiation to a target;

a focusing beam collection system for collecting said focusing radiation after reflection from the target; and a focus detection system for receiving the collected focusing radiation and for processing the collected focusing radiation to determine whether the optical system is in focus with respect to the target;

wherein the focus monitoring arrangement further comprises a reference beam delivery system for delivering to said focus detection system reference radiation, the reference radiation being arranged to interfere with the collected focusing radiation in said focus detection system, wherein the reference radiation and focusing radiation are provided with at least one relative frequency shift so that the interfering radiation detected in the detection system includes a time-varying component having a characteristic frequency corresponding to the or each relative frequency shift, and wherein the focus detection system comprises one or more lock-in detectors operable with reference to said characteristic frequency.

Using the lock-in detector, the desired focusing radiation can be separated with high quality from other signals in the optical system.

The focus monitoring arrangement may be provided as part of a functional apparatus of which the same optical system is a part. Alternatively, the focus monitoring arrangement may be coupled to a functional apparatus and used for controlling operation of the other apparatus.

In a particular embodiment, the focusing radiation comprises first focusing radiation having a first wavelength range and second focusing radiation having a second wavelength range. The reference radiation comprises first reference radiation having substantially the first wavelength range and second reference radiation having substantially the second wavelength range. The first reference radiation and first focusing radiation are provided with a first relative frequency shift and the second reference radiation and second focusing radiation are provided with a second relative frequency shift so that the interfering radiation detected in the detection system includes a first time-varying component having a characteristic frequency corresponding to the first relative frequency shift and a second time-varying component having a characteristic frequency corresponding to the second relative frequency shift.

In such an embodiment, the focus detection system may comprise one or more lock-in detectors operable with reference to both the first and second characteristic frequencies and is operable to select which of the first and second focusing radiation is used to determine whether the optical system is in focus.

The lock-in detectors may be based on spectral analysis of a sampled signal obtained using a high-speed photodetector. Alternatively, a lock-in image detector may be used to capture an image field using radiation only of the selected the characteristic frequency.

The invention further provides an inspection apparatus comprising an inspection illumination system for delivering inspection radiation to the target and an inspection detecting system for collecting the inspection radiation after being scattered by the target, wherein an optical system that forms part of one or both of the inspection illumination system and inspection detection system is provided with a focus monitoring arrangement according to the invention as set forth above.

These and further features and advantages of the invention will be apparent to the skilled reader from a consideration of the detailed description of examples that follows.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Figure 1:
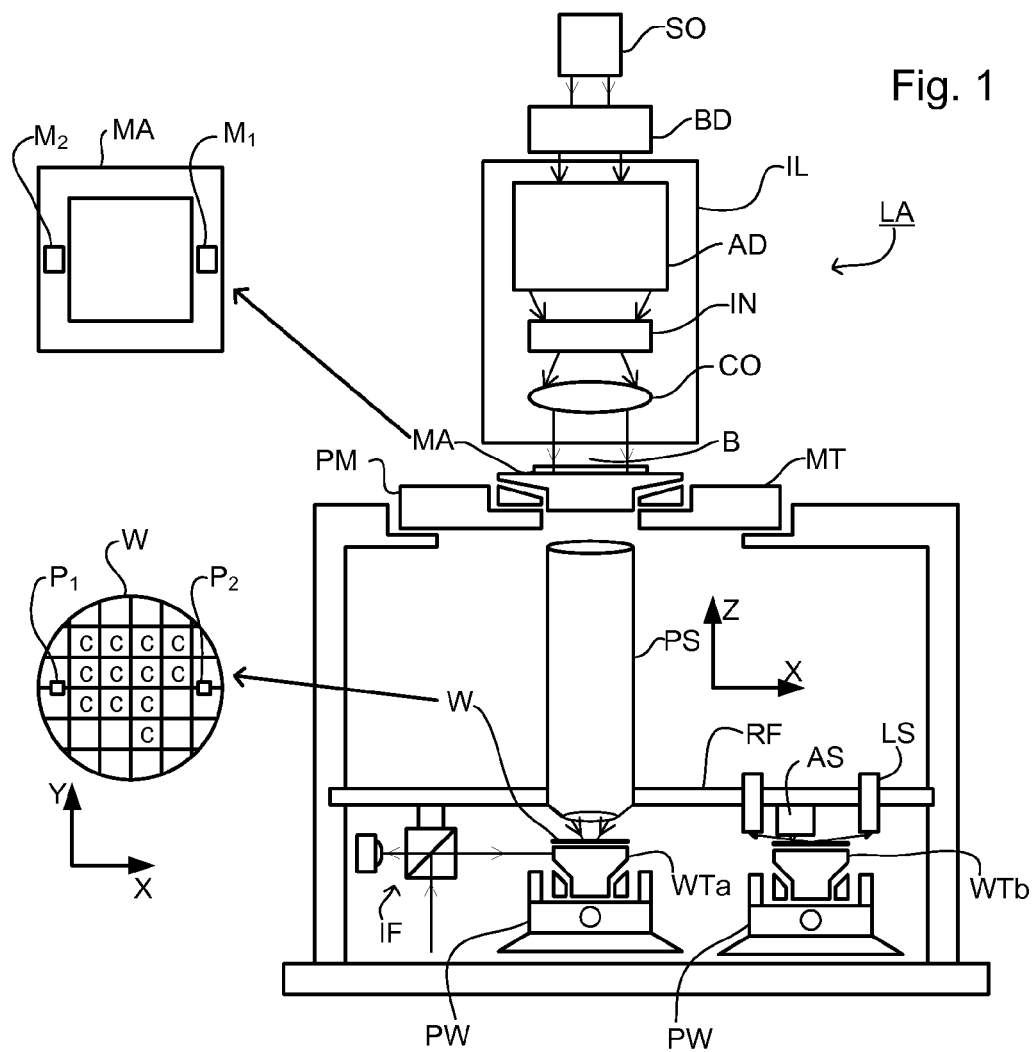
FIG. 1 depicts a lithographic apparatus.

FIG. 1 schematically depicts a lithographic apparatus. The apparatus comprises:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
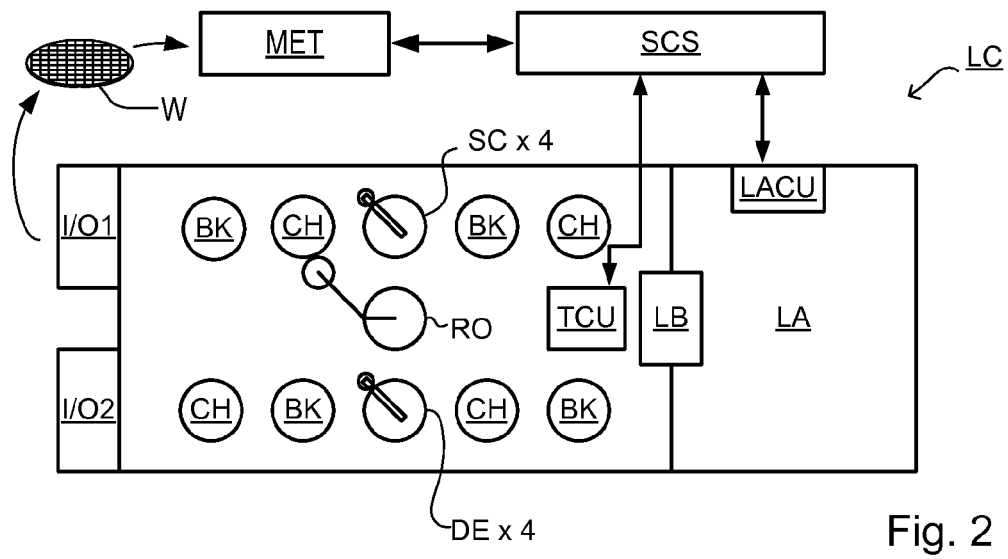
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
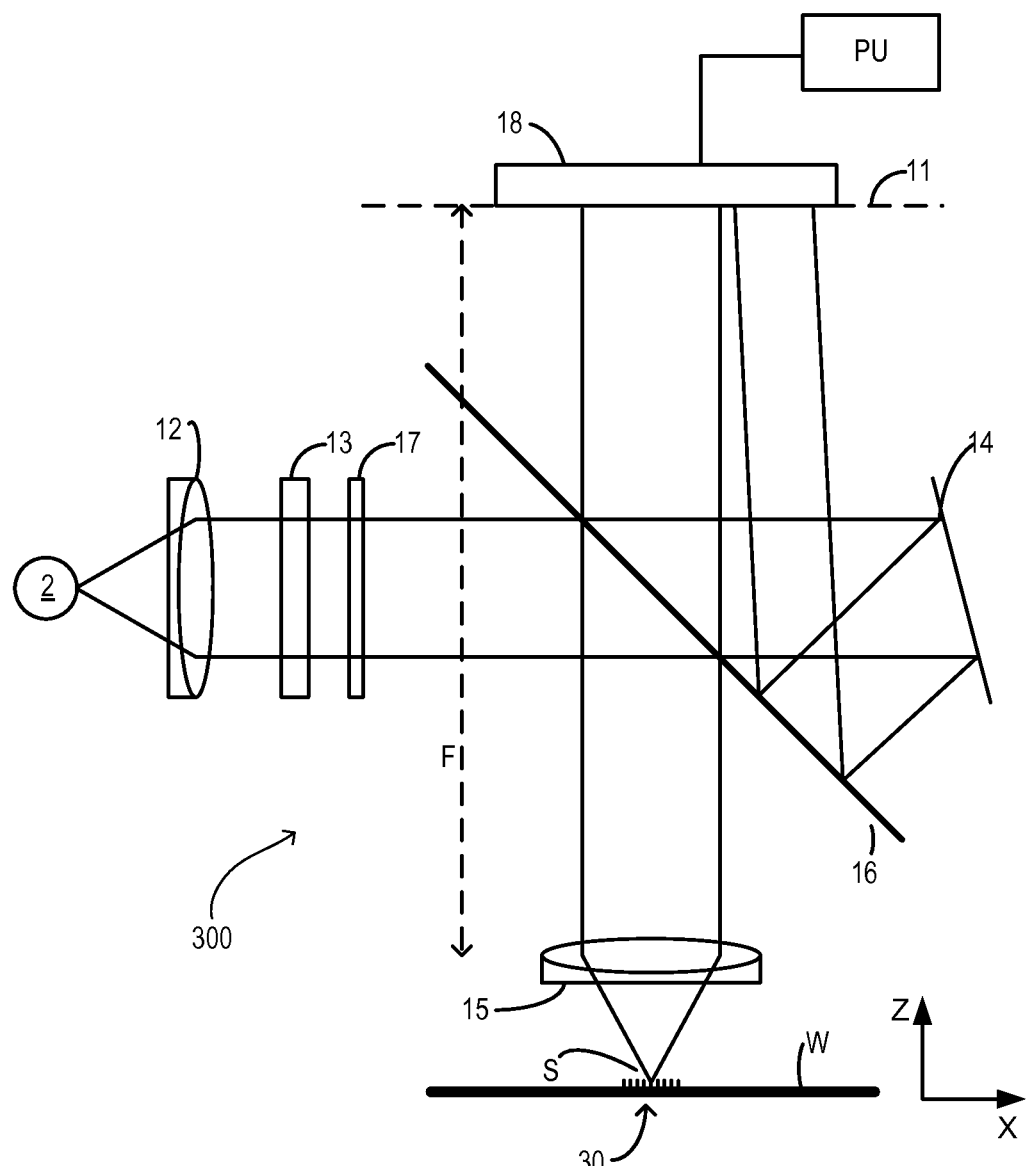
FIG. 3 depicts a known inspection apparatus arranged to perform angle-resolved scatterometry, as an example of an optical system in which a focus monitoring arrangement according to the present invention may be applied.

FIG. 3 depicts a known scatterometer 300. In this device, the radiation emitted by radiation source 2 is collimated using lens system 12 and transmitted through interference filter 13 and polarizer 17, reflected by partially reflecting surface 16 and is focused into a spot S on substrate W via a microscope objective lens 15, which has a high numerical aperture (NA), preferably at least 0.9 and more preferably at least 0.95. Immersion scatterometers may even have lenses with numerical apertures over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate tables. Coarse and fine positioners may be provided to a second positioner PW configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle which one of those is moving in the real world, r if both are moving.

The reflected radiation then passes through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters. An aperture stop or spatial light modulator (not shown) may be provided in the illumination path to control the range of angle of incidence of radiation on the target.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processor PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of for instance FIG. 3 are described for example in published patent application US2006066855A1. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 3, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

Figure 4:
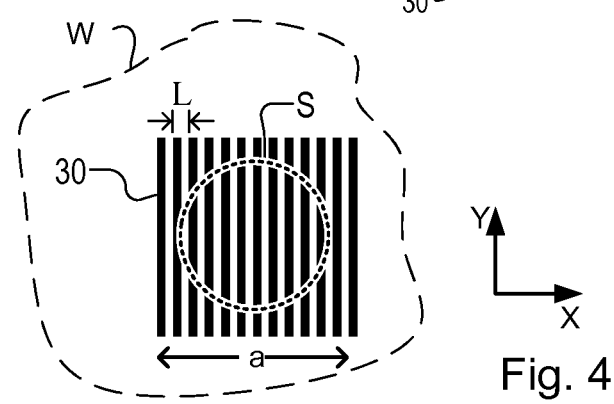
FIG. 4 illustrates the relationship between an illumination spot and a target grating in an example of the known scatterometers.

FIG. 4 illustrates a plan view of a typical target 30, and the extent of illumination spot S in the scatterometer of FIG. 3. To obtain a diffraction spectrum that is free of interference from surrounding structures, the target 30 in the known method is a grating larger than the diameter of the illumination spot S. The diameter of spot S may be over 10 or 20 µm and the grating width and length may be 30 or 40 µm square. The grating in other words is 'underfilled' by the illumination, and the diffraction signal is free from interference by product features and the like outside the target grating itself. The illumination arrangement 2, 12, 13, 17 may be configured to provide illumination of a uniform intensity across a pupil plane of objective 15. Alternatively, but including an aperture in the illumination path, illumination may be restricted to on axis or off axis directions. As described in prior applications cited above, a modified scatterometer can use so-called dark field imaging to capture diffracted radiation from several smaller targets, all falling within the same illumination spot S.

Focus Monitoring Using Interferometry and Lock-In Detectors

Regardless of the type of inspection apparatus, or other optical system, it is general required to provide an automatic system for monitoring and adjusting focus of an optical system such as the system that forms the scatterometer in FIG. 3. If the spot S is not focused, then the illumination will fall on features other than the target 30, and the collected radiation will not allow an accurate measurement of the properties of the target. As mentioned already, focusing arrangements are known which pass a beam of radiation through the optical system and use some kind of detector system to obtain a signal representing focus error. for example in published patent application US20080151228A. Light reflected from the target is imaged onto two photodetectors with different focus offsets. Comparing the focused spot area between the two photodetectors allows an indication of defocus of the optical system to be obtained, and the direction of defocus to be identified. The US patent application illustrates various simple photodetectors that may be used to obtain a measure of spot area. Other types of focus arrangement can be envisaged, and the present disclosure is not limited to the technique of US20080151228A Disclosed herein is a modified focus monitoring arrangement and associated method in which lock-in detectors are used to monitor focus related properties of an exposure apparatus using a heterodyne interferometric technique. The focus monitoring arrangement is intended to be used in an optical system such as the inspection apparatus described above.

Figure 5:
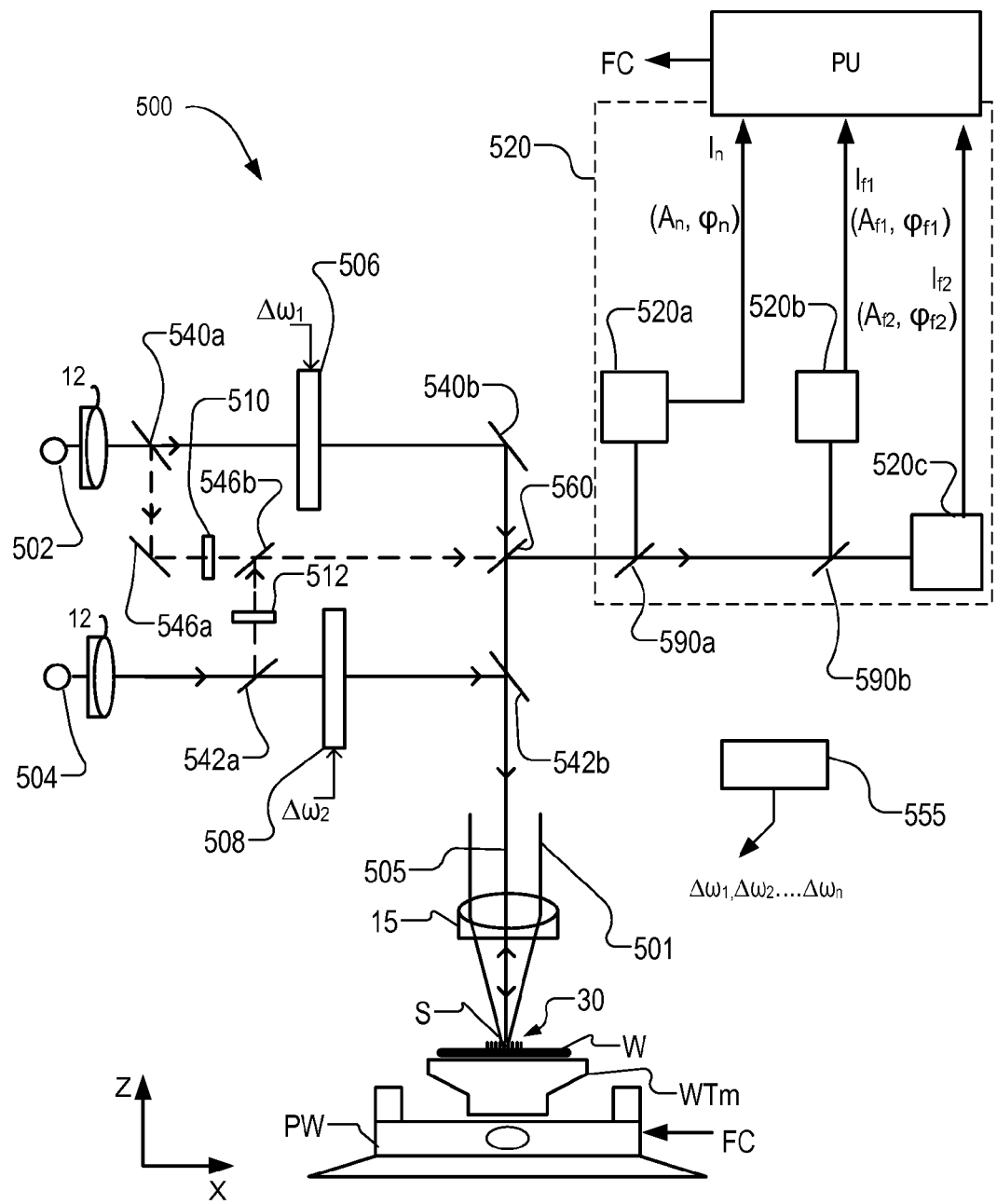
FIG. 5 is a schematic diagram of a focus monitoring arrangement in an inspection apparatus including lock-in detectors according to an embodiment of the invention.

FIG. 5 depicts in a simplified form a focus monitoring arrangement 500 implementing an heterodyne interferometric technique. FIG. 5 in particular provides a schematic view of optical paths for use in determining and controlling focus related properties of an inspection apparatus. With regard to the main function of the optical apparatus as a scatterometer or other inspection apparatus, a measurement illumination beam labeled 501 follows an illumination path comprising optical components 12, 13, 16, 17 (not shown in this drawing) and objective lens 15 (shown). A collection path comprising 15 for collecting radiation reflected by target 30 is also provided, as described above with reference to FIG. 3. The radiation collected by optical components of the collection path is directed to a detector 18 connected to processor PU for target reconstruction or other purposes. The form and function of these may be the same as described above with reference to FIG. 3, and thus will not be discussed in this section. Target 30 may be formed on a substrate W that has been patterned and processed using the lithographic apparatus of FIG. 1 and the cluster of processing tools described above with reference to FIG. 2. The optical system including objective lens 15 is mentioned for the same of example only. It may be adapted for dark field imaging instead of or in addition to angle resolved scatterometry.

The focus monitoring arrangement and methods illustrated and described below can be applied in an optical system designed for a different kind of inspection (for example in a microscope), or for a purpose different from inspection (for example surface treatment, or optical recording). In particular, the arrangements of the present disclosure can also be applied to focusing of the projection system PS in the lithographic apparatus LA, or ancillary systems such as the alignment sensor AS. Indeed the optical system of the focus monitoring arrangement may or may not be part of (or share parts with) a functional optical system that is performing inspection or treatment of a target. The optical system of the focus monitoring arrangement may be ancillary to another functional system which is monitored and/or controlled indirectly using focusing of the optical system of the focus monitoring arrangement. In these cases, the optical system through which focusing is monitored is not the same as the functional system performing inspection and/or processing of the target. In the field of lithography, for example, the functional system may be an electron beam (e-beam) patterning apparatus, such as are used to make the reticle (patterning device) M. Other examples may be laser or mechanical machining or surface treatment apparatuses. Provided the focus monitoring arrangement is coupled to and calibrated with the functional system, a desired monitoring and/or control function may be implemented.

Focusing of the illumination spot S on target 30 is achieved by a suitable mechanism which may involve moving elements within the optical system, and/or moving the optical system and substrate bodily in relation to one another. For the sake of example in this illustration, substrate W is supported by a substrate table WTm similar to the substrate tables WTa and WTb of the lithographic apparatus. Positioners PW control the height of the substrate in response to a focus control signal FC generated by processor PU. Positioners PW control the position of substrate W in X and Y directions also, to bring each target of interest into position beneath the objective lens 15.

Focus monitoring arrangement 500 in this example comprises a first radiation source 502, a second radiation source 504, each with an associated lens system. Focusing radiation 505 passes through objective lens 15 to be reflected from target 30. The arrangement further includes a first frequency shifter 506, a second frequency shifter 508, a first attenuating device 510, a second attenuating device 512 and a focus detection system 520 including a normalization signal detector 520a and first and second lock-in detectors 520b and 520c. These components are arranged in an optical system which defines effectively several optical paths. Generally speaking, as in a known apparatus, there is an illumination system for illuminating the target with focusing radiation 505 and a collection system for collecting reflected radiation and delivering it to detection system 520. More specifically, arrangement 500 comprises a first illumination path, delivering a first focusing radiation to the objective lens and the target. The first illumination path includes radiation source 502, first frequency shifter 506 and optical components 540a (e.g. beam splitter) and 540b (e.g mirror). Further, the arrangement 500 includes a second illumination path, delivering second focusing radiation to objective lens and the target. The second illumination path includes second radiation source 504, second frequency shifter 508 and optical components 542a (e.g. a beam splitter) and 542b (e.g. a mirror). As explained further below the first and second focusing radiation differ in their color (wavelength range). First focusing radiation has a first wavelength range and second focusing radiation has a second wavelength range.

Additionally, there is provided a heterodyne reference system, exploiting the frequency shifts introduced by frequency shifters 506, 508, as explained below. The reference system includes a first reference path, delivering first reference radiation to the detection system 520, bypassing the objective lens and target. The first reference path includes first attenuating device 510 and optical component 546a (e.g. a mirror) as shown. Similarly a second reference path is provided for delivering second reference radiation to the detection system 520. The second reference path includes second attenuating device 512 and optical component 546b (e.g. a mirror). The collection system, defining a collection path for the focusing radiation 505 after it is reflected from target 30, comprises objective lens 15 and optical component 560 (e.g. a mirror).

A frequency source 555 provides first and second reference frequencies $\Delta\omega_1$ and $\Delta\omega_2$ to the first and second frequency shifters 506 and 508, respectively. A selected one of these reference frequencies is also provided to the first and second lock-in detectors 520b and 520c. These detectors may be single pixel photodiodes, or multi-pixels or multi-zone detectors, as described in the prior patent application mentioned above. Detection system 520 includes processor PU receives data from detectors 520a, 520b, 520c and uses these to generate focus control signal FC. It may be envisaged that a processor PU is implemented by software sharing the same processing hardware as processor PU shown in FIG. 3 for the metrology functions. However, a dedicated sub-processor can be provided to implement the focus monitoring and control functions, if desired.

The mentioned beam paths can be implemented in many different layouts, and a particular configuration of mirrors 540b, 542b, 546a, 546b and 560 and beam splitters (BS) 540a, 542a is shown schematically here, only for illustration of the principles of the design. Not shown in the drawing are numerous components that would be included in a practical system, including for example lenses or other focusing elements. These can be adapted readily from the known apparatus and do not need to be described in detail. Additional beam paths for different functions (for different types of measurement) can also be provided.

Figure 6:
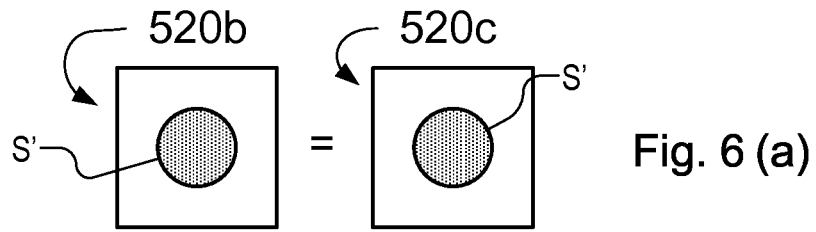
FIGS. 6a-6c illustrates a principle of focus determination in the focus monitoring arrangement of FIG. 5.
Figure 6:
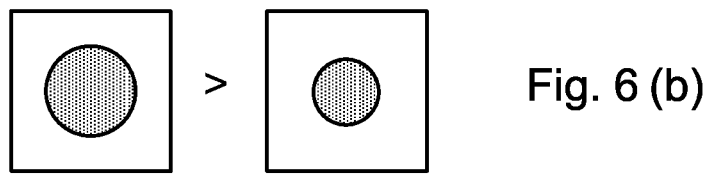
Figure 6:
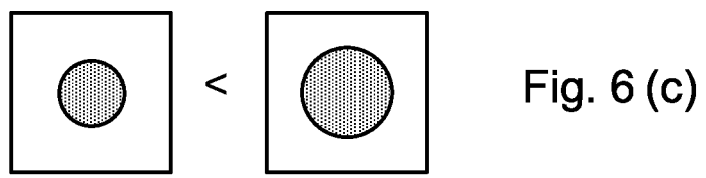

Referring briefly to FIG. 6, it may be recalled that a focus measurement can be derived by comparing the size of a radiation spot as seen by two detectors 520b and 520c. The principles of this technique, as well as some variations that may be applied equally in the present arrangement, are described in the prior patent application US20080151228A, mentioned above. In this arrangement, the two detectors are arranged one in front and one behind a back focal plane of the optical system, also referred to as a field plane. That is to say, the two detectors are deliberately positioned to experience focus errors when the optical system is actually focused on the target. This deliberate defocus, as well as any actual focus error, influences the size of spot image S' on each detector. When focus error is zero, spot images S' on both detectors will be equal (FIG. 6 (a) situation). When focus error is non-zero in a first direction, spot image S' will spread over a greater area on detector 520b and a smaller area on detector 520c (FIG. 6 (b) situation). This inequality of spatial extent (which may be measured in various ways) can be detected electronically. Similarly, when focus error is non-zero in an opposite direction, spot image S', the inequality will be reversed (FIG. 6 (c) situation). These detected inequalities can be used to generate a focus error measurement, and/or a correction in the focus control signal FC.

Figure 7:
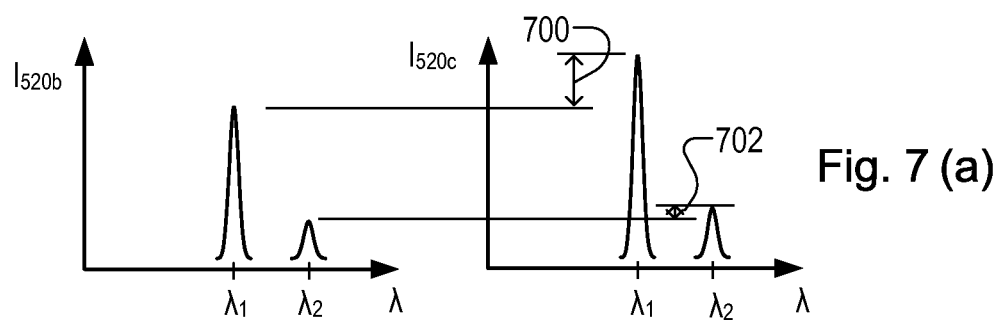
FIGS. 7a-7b shows how focus signals at different optical wavelengths may be suitable for focus monitoring on different targets.
Figure 7:
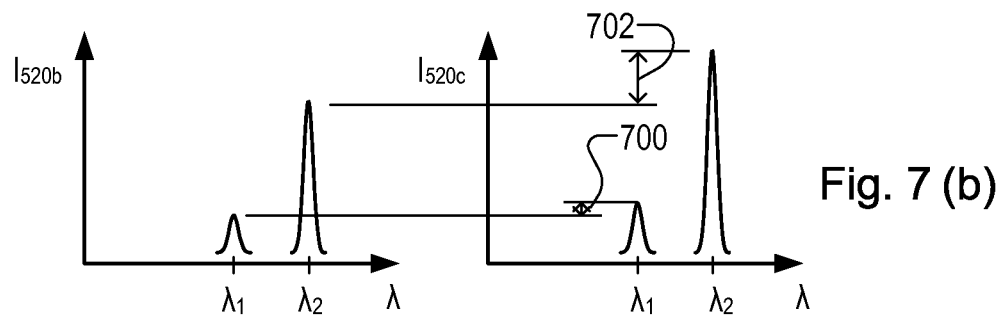

FIG. 7 illustrates problems of focus detection in different targets (substrates). These targets may be different because of geometry (layer thicknesses) and/or material (refractive index variations). FIG. 7(a) illustrates, for a first target T, focus detection signal that may be obtained from the detectors at different optical wavelengths λ. Using a monochrome focusing radiation at wavelength $\lambda_1$, reflected signals received at detectors 520b and 520c are strong. An inequality 700 can be clearly observed and used to measure focus error. Using a different wavelength $\lambda_2$, signals are less strong. An inequality 702 can be measured, but it is much more susceptible to noise. Clearly, for this target, the wavelength $\lambda_1$ should be preferred for use in the focus monitoring arrangement.

However, for a different target structure (FIG. 7(b)), the reflected signal strength at wavelength $\lambda_1$ may be much less than it would have been at wavelength $\lambda_2$. In one aspect, the present disclosure addresses this problem by providing a focus monitoring arrangement that can operate at two or more wavelengths without interference between the wavelengths, and without interference with other optical signals that may be present. These multiple wavelengths can be generated and separated without moving parts. They may be generated simultaneously and selected either one at a time or simultaneously, depending on the implementation.

Referring again to FIG. 5, it will now be explained how this desired selectivity of wavelength is obtained in the focus monitoring arrangements according to the present disclosure.

First focusing radiation collected from the target mixes with the first reference radiation. If these two beams are coherent at the detectors 520b, 520c they will interfere in a well-defined manner. Similarly the second focusing radiation and the second reference radiation interfere in the detection system. Radiation sources 502 and 504 may each be a monochromatic coherent light source (e.g. a narrow linewidth laser). By using a coherent light source, the apparatus becomes less sensitive to differences in the optical path length between the focusing radiation and the reference radiation and interferometric measurements using detectors 520b, 520c become feasible.

The skilled person will understand that coherence between different beams of radiation derived from a common source depends on spatial coherence and temporal coherence of the source radiation. Temporal coherence can be expressed in terms of coherence time but is commonly expressed in terms of coherence length (these are related simply by the speed of light in whatever is the transmitting medium). Two interfering rays will be coherent where the path lengths that they have followed are the same within a coherence length of the source radiation. The phase relationship between the waves in the two paths will be fixed. A monochromatic laser is considered a coherent light source because produces radiation having a coherence length much longer than any distances found in a practical optical system. However, even though broadband radiation will normally be considered to be incoherent light, it still has a (small) coherence length, related to its spectral bandwidth. Spatial coherence refers to coherence across a beam of radiation (across a wave front), rather than longitudinally. In order to obtain useful interference between two beams derived from a common source, the spatial shift at each point in the beam should be within a coherence area of a the corresponding point in the other beam.

Incoherent light sources (and additional components such as for example optical filters) could be used in the optical arrangement of FIG. 5, provided that the path length differences are made negligible (that is, shorter than the coherence length of the used radiation). This constraint may bring challenges in the design. On the other hand, it brings a wider choice of radiation source, and it avoids the need to manage "speckle" which arises when using spatially coherent sources.

While the frequency shifters are shown in the paths of the focusing radiation, they could alternatively be provided in the paths of reference radiation instead. The beams delivered by radiation sources 502 and 504 could in principle be delivered by a same source coupled to optical components used to selected required wavelengths. Further, more than two radiation sources can be implemented in inspection apparatus 500 of FIG. 5. Additional beam paths and optical components for different functions may also be provided.

Attenuating devices 510 and 512 may be for instance neutral density filters. Attenuating devices 510 and 512 may be placed somewhere else in the reference paths to adjust the intensity of the reference beams delivered by the radiation sources 502 and 504 to be compatible with the intensity of the reflected radiation in a particular case. The degree of attenuation can be made variable. For example by a motorized neutral density filter wheel.

A frequency shifter may be for example an electro-optic modulator, a fiber modulator, a magneto-optical modulator, a modulator based on Zeeman Effect and/or an acousto-optic modulator. For the sake of example, frequency shifters 506, 508 may be acousto-optic modulators (AOMs).

As known by persons skilled in the art, an AOM operates by setting up acoustic waves in a crystal. These waves form a kind of moving Bragg grating within the crystal, with a speed of movement determined by the driving frequency. Incident light (at a frequency ω) focused onto the AOM in the Bragg regime (to satisfy the Bragg condition), is mainly diffracted into a first order output beam and a zero order output beam, separated by twice the acoustic Bragg angle. The motion of the "grating" within the AOM also causes the frequency of the first order output beam to be frequency-shifted by ω+mΔω, with m=1 corresponding to the first order diffraction and Δω the modulation frequency. For the first order diffracted light, the frequency shift of the frequency is equal to the modulation frequency of the AOM. The frequency shifters (AOMs) 506, 508 may be driven by frequency source 555 at different modulation frequencies, such that for example $\Delta\omega_1$ may be 30 kHz $\Delta\omega_2$ may be 100 kHz. Such a small shift in frequency (small relative to the frequency of radiation at or around visible wavelengths) has no impact on scattering/diffraction effects at the target. The exact frequency and phase of the frequency source is unimportant, so long as the lock-in detectors are locked at frequencies corresponding to the beat frequencies of interest.

Detectors 520b and 520c of detection system 520 are in the present example lock-in detectors. Lock-in detection is known generally as a technique that can perform narrow-band (thus low noise) detection by 'tagging' part of the signal with a periodic variation that contains desired information. The signal of interest is tagged by modulating the signal at a chosen frequency $\omega_D$, for example. A lock-in sensor is locked at the chosen frequency $\omega_D$ to record the signal of interest and to ignore other signals, or noise. In order to 'tag' focus monitoring signals in the present apparatus, relative frequency shift is applied between the radiation in the illumination beams and the reference beams. A beat frequency arises when the beams interfere. The beat frequency, equal to the relative frequency shift, is used as the lock-in frequency for the lock-in detectors. Moreover, by tagging the first focusing radiation and the second focusing radiation with different beat frequencies (different periodic components), they can be detected separately from one another, as well as separately from any noise. Using different frequency shifts $\Delta\omega_1$ and $\Delta\omega_2$ of the first and second focusing radiation relative to the first and second reference radiation, lock-in detectors 520b, 520c can be made selectively responsive to only the first focusing radiation or only the second focusing radiation. If the lock-in detection is synchronized with the frequency source 555, a very high selectivity and can be obtained, and phase information can be extracted as well.

Figure 8:
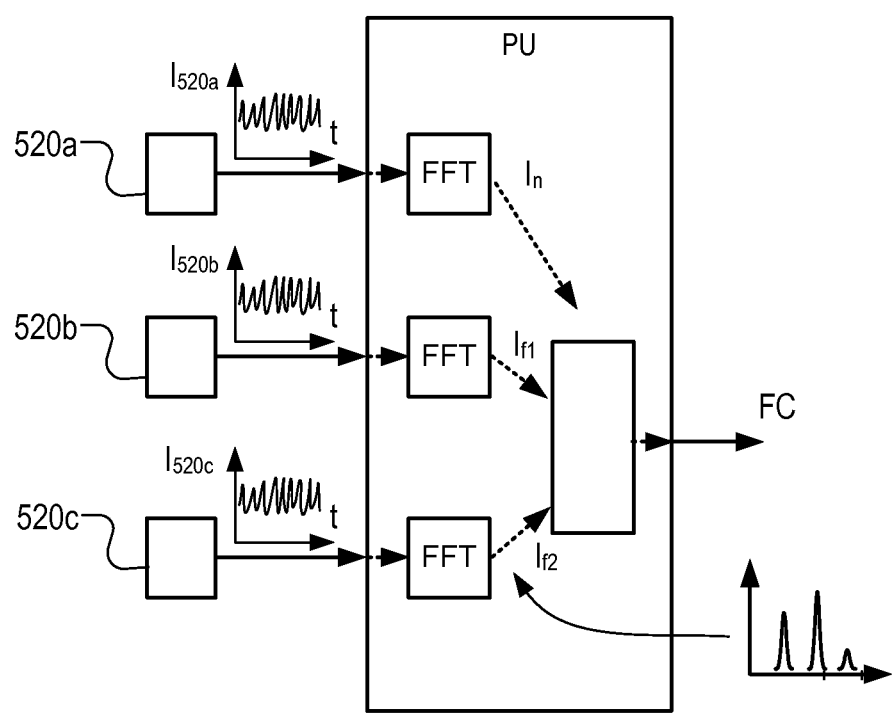
FIG. 8 illustrates the principle of operation of a lock-in detectors in one embodiment of the apparatus of FIG. 5.

FIG. 8 illustrates a possible implementation of signal processing in focus detection system 520 in the arrangement of FIG. 5. The individual detectors 520a, 520b, 520c are in this example simple high-speed photodiodes. In order to be able to measure (indirectly) the size of spot, a mask or aperture smaller than the expected spot can be placed in front of the photodiode (or the photodiode sensitive area can be made small in itself. Then, while the spot grows, the detected intensity on the sensitive area of the photodiode will actually reduce. This is only one possible implementation.

If each detector 520b and 520c is in fact segmented into multiple pixels or regions, then each region will yield a signal $I_{f1}$ or $I_{f2}$. Putting it another way, each of the signals $I_{F1}$ and $I_{f2}$ may in some embodiments comprise multiple components, each relating to a different region of the corresponding detector. In the following description of a first embodiment, only a single component is mentioned, for the sake of simplicity, the same discussion applying to each of the pixel regions. The third detector 520a is provided to measure a normalization signal $I_n$, representing the intensity of the illumination beam. In an alternative embodiment, each detector is an image detector comprising an array of many pixels.

Small graphs in FIG. 8 show the temporal evolution of an illumination intensity I(t) recorded by each detector 520a, 520b, 520c. A conventional detector, such as detector 520a would simply integrate this intensity for an exposure interval, and output a single intensity measurement. In lock-in detectors, however, the radiation is sampled over time in such a way that specific periodic components can be identified and measured separately. In this particular example, the time-varying signal from each photodiode is sampled at high frequency (for example greater than 100 kHz, greater than 200 kHz, for example in the range 300-500 kHz) and digitized. The digitized signals are then processed by processor PU (or by a dedicated digital signal processor (DSP)) to identify periodic components of interest. The periodic components may be identified by calculating frequency spectrum of the photodiode signals, for example using fast Fourier transform (FFT) algorithms. An FFT will deliver a complete spectrum of the signals, The theory of this lock-in detection will be described in more detail below.

In this way, first lock-in radiation detector 520b measures a first focus signal, for example one or more intensity values $I_{f1}$ while second lock-in detector 520c measures a second focus signal $I_{f2}$.

Detector 520a, 520b, 520c may for example a photodiode device and/or adapted (i.e. lock-in) photodiode devices. Note that adapted CMOS image sensor, single-photon avalanche diodes (SPADs), CCDs or any other suitable sensors may also be used as detectors. Readers skilled in the art will be able to adapt known lock-in methods and/or phase-sensitive detection methods to detect amplitude and phase images as described herein. Using lock-in functionality, amplitude and phase values (A, φ) can be calculated and used if desired, not only intensity. The phase of the measured signal could be used for example to determine depth of focus inside the target. The detailed operation of the lock-in functions will now be described, with mathematical basis.

Returning to FIG. 5, the following describes the processing of the first focusing radiation and first reference radiation delivered by radiation source 502 for simplicity. Optical paths and functions of the second focusing radiation and second reference radiation delivered by radiation source 504 are similar.

Radiation emitted by radiation source 502, emitting monochromatic radiation of frequency $\omega_1$, is split in two paths (the first illumination path and the first reference path) by beam splitter 540a. The first illumination path includes frequency shifter 506 that shifts the frequency of the first illumination beam to a frequency $\omega_1+\Delta\omega_1$. The focusing radiation of frequency $\omega_1+\Delta\omega_1$ is directed to target 30 by optical component 540b through optical components 560 and 542b and through objective lens 15. Objective lens 15 in the case of the known type of scatterometer has a high numerical aperture (NA), preferably at least 0.9 and more preferably at least 0.95. Using immersion techniques the scatterometer may even have lenses with numerical apertures over 1. The first focusing radiation (at frequency $\omega_1+\Delta\omega_1$) is reflected by the target on substrate W and collected by objective lens 15 and directed back to optical component 560 through optical component 542b. Optical component 560 directs the reflected radiation to detection system 520.

In a situation where lock-in detectors 520b and 520c are locked to the same frequency $\Delta\omega_1$, they will detect selectively the interference between the first focusing radiation and the first reference radiation. All other signals and frequencies will be discarded as noise. The signals $I_n$, $I_{f1}$, $I_{f2}$ detected by detectors 520a, 520b, 520c are output to processor PU, and used to determine focus error using the first wavelength of radiation. By locking to a different frequency $\Delta\omega_2$, focus error can be determined using the second wavelength of radiation. As will be described below, in some embodiments the detectors can lock into two different frequencies simultaneously, so that the arrangement can use either or both wavelengths.

In addition to providing selectivity between two different wavelengths, the use of lock-in detection improves signal to noise ratios of the focus determination. The mathematical basis of this will now be explained. Recall that the first reference radiation, following the first reference path, is directed to detection system 520 by optical component 546a through first attenuating device 510 and optical components 546b, 560. The first reference radiation at frequency $\omega_1$ interferes with collected first focusing radiation at relatively shifted frequency $\omega_1+\Delta\omega_1$. These two interfering radiations, which are coherent with one another, generate a 'beat' signal. The interfered radiation carrying the beat signal is divided by optical component 590a (e.g. a beam splitter) into two parts. A first part is directed to detector 520a and a second part is further divided into two parts by optical component 590b (e.g. a beam splitter). One of these parts is directed to lock-in detector 520b and a second one of these parts is directed to lock-in detector 520c. In this configuration, the signal $I_n$ detected by detector 520a may be used for intensity normalization.

The information associated to the signal are encoded in the intensity signal detected by each of the detector. Ignoring again the second radiation from source 504 and considering only the first radiation at the first wavelength the optical field $(E_T)$ of amplitude $|E_T|=\sqrt{I_T}$, oscillating at an (angular) frequency $\omega_1+\Delta\omega_1$, reflected by target 30, the field can be expressed as $E_T=|E_T|e^{i\varphi(t)}e^{i(\omega_1+\Delta\omega_1)t}$, with $|E_T|$ the field amplitude, $I_T$ the intensity reflected by the target, $\varphi(t)$ represents a phase term. Similarly, the optical field $E_R$ of amplitude $|E_R|=\sqrt{I_R}$ and angular frequency $\omega_1$ associated with radiation source 502 can be expressed as $E_R=|E_R|e^{i(\omega_1)t}$. The total intensities of the radiation reaching each of the detectors of detection system 520 can be expressed as follows:

At detector 520a:     (1)
$$I_{520a} = R_{590a} \times \lfloor |E_T|^2 + |E_R|^2 + 2|E_T||E_R|e^{i\varphi(t)}e^{i(2\omega_1+\Delta\omega_1)t} + 2|E_T||E_R|e^{-i\varphi(t)}e^{i(\Delta\omega_1)t} \rfloor + \sum_{0}^{\infty} N_{520a}(\omega),$$

At detector 520b:     (2)
$$I_{520b} = (1-R_{590a}) \times R_{590b} \times \lfloor |E_T|^2 + |E_R|^2 + 2E|E_T||E_R|e^{i\varphi(t)}e^{i(2\omega_1+\Delta\omega_1)t} + 2|E_T||E_R|e^{-i\varphi(t)}e^{i(\Delta\omega_1)t} \rfloor + \sum_{0}^{\infty} N_{520b}(\omega),$$

At detector 520c:     (3)
$$I_{520c} = (1-R_{590a}) \times (1-R_{590b}) \times \lfloor |E_T|^2 + |E_R|^2 + 2|E_T||E_R|e^{i\varphi(t)}e^{i(2\omega_1+\Delta\omega_1)t} + 2|E_T||E_R|e^{-i\varphi(t)}e^{i(\Delta\omega_1)t} \rfloor + \sum_{0}^{\infty} N_{520c}(\omega),$$

In the above equations, $R_{590a}$ and $R_{590b}$ are reflection coefficients of optical components 590a and 590b respectively and $$\sum_{0Hz}^{\infty} N_{520a/b/c}(\omega)$$

represent total measurement noise terms at detectors 520a/b/c over the entire frequency spectrum of the focus monitoring arrangement. The frequency spectrum of the arrangement is ultimately determined by the electronic bandwidth of the detectors 520a, 520b, 520c. This bandwidth may be for example greater than 100 kHz or even 200 kHz. In an example implementation, the detectors comprise high-speed photodiodes with a sampling frequency of around 400 kHz.

As can be seen from equations (1) to (3), the signals at each of the detectors contain several components such as a DC component ($|E_T|^2+|E_R|^2$) in addition to measurement noise terms integrated over the entire frequency spectrum of the system. As known by persons skilled in the art, the noise spectral density is generally proportional to 1/f (with f a frequency), so that the noise energy falls with increasing frequencies. Only components of equations (1) to (3) having an angular frequency $\Delta\omega_1$ (for example the term $2E_T E_R e^{-i\varphi(t)}e^{i(\Delta\omega_1)t}$) contain information relevant to the determination and control of the focus properties. Further, as explained above, if each of the detectors of detection system 520 is locked at a frequency $\Delta\omega_1$, only periodic components synchronized with frequency $\Delta\omega_1$ may then be detected by the detectors. These detected periodic components will thus be:

At detector 520a:

$$I_n = R_{590a} \times \lfloor 2|E_T||E_R|e^{-i\varphi(t)}e^{i(\Delta\omega_1)t} \rfloor + N_{520a}(\Delta\omega_1)$$ (4), At detector 520b:

$$I_{f1} = (1-R_{590a}) \times R_{590b} \times \lfloor 2|E_T||E_R|e^{-i\varphi(t)}e^{i(\Delta\omega_1)t} \rfloor + N_{520b}(\Delta\omega_1)$$ (5), with $R_{590a}$ the reflection coefficient of optical component 590a.

At detector 520c:

$$I_{f2} = (1-R_{590a}) \times (1-R_{590b}) \times \lfloor 2|E_T||E_R|e^{-i\varphi(t)}e^{i(\Delta\omega_1)t} \rfloor + N_{520c}(\Delta\omega_1)$$ (6), with $N_{520a/b/c}(\Delta\omega_1)$ total measurement noise terms at detectors 520a/b/c generated at frequencies around the lock-in frequency.

A key feature of the above heterodyne interferometric technique is the significant increase of the sensitivity of the detection system. This results in an improved signal to noise ratio, because only noise generated at frequencies around the lock-in frequency can be seen in equations (4) to (6). As a direct consequence to the reduction in the noise level, the detection system becomes more robust and/or allows implementation of a low intensity focus monitoring arrangement. As mentioned, the same equations and reasoning apply to the second focusing radiation and second reference radiation, when the detection is locked in to frequency $\Delta\omega_2$. Moreover, by being able to select the lock-in frequency, focus monitoring can be performed using whichever of the first wavelength and second wavelength yields the stronger signals on a given target. Both wavelengths can be applied simultaneously without blending of the wavelengths. A voting mechanism in the software can be used to select the best signal of the two (or more) to determine optimum focus. A weighted combination of the two could be used to select how much each wavelength influences a final result, rather than a simple selection.

Additionally, an increase in the detection system dynamic range is further achieved by controlling the intensity of the first reference beam delivered by the radiation source 502 via attenuating device 510. For example, if the intensity level of the radiation reflected by target 30 is high at the currently selected wavelength, the intensity level of the first reference beam can be decreased while still maintaining the high sensitivity of the detection system. If, on the other hand, the intensity level of the radiation reflected by target 30 falls below a threshold intensity level required by the detection system to operate then the intensity level of the first reference beam can be increased by the required amount by activation of the attenuating device 510. Processor PU can be connected to actuators (not shown) to control the attenuating devices 510 and 512 automatically as required.

The inventors have calculated that dynamic range improvement by a factor up to $10^6$ may be achieved by application of the techniques disclosed herein. Of this improvement, up to $10^4$ times is a result of using interferometric noise reduction (frequency shifts and lock-in detection) and another $10^2$ times results from use of an adjustable attenuating device. Consequently, where a current focus monitoring arrangement may require a power of radiation reflected by a target be of the order 1 μW, a reflected power of the order of 100 nW down to 1 pW may be sufficient while maintaining a high detection system sensitivity.

Further, as mentioned, part of the interfering radiation may be used for intensity normalization. For instance, the signal $I_n$ recorded by detector 520a may be applied as an intensity normalization factor to the signals recorded by detectors 520b and 520c. Intensity normalization may be a first step of data processing performed in detectors 520b and 520c or within the processor unit PU.

Figure 9:
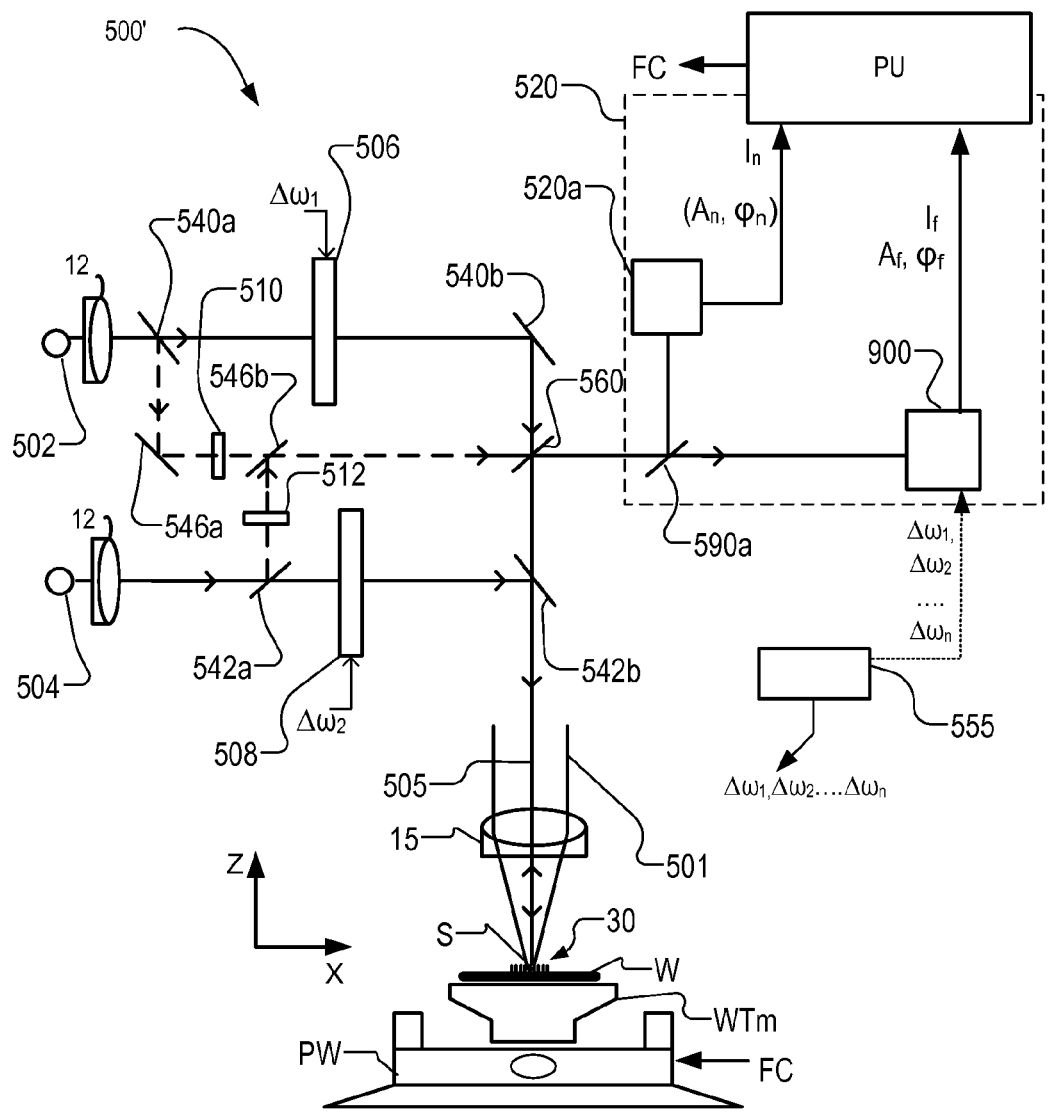
FIG. 9 is a schematic diagram of a focus monitoring arrangement in an inspection apparatus including a lock-in image detector according to an alternative embodiment of the invention.
Figure 10:
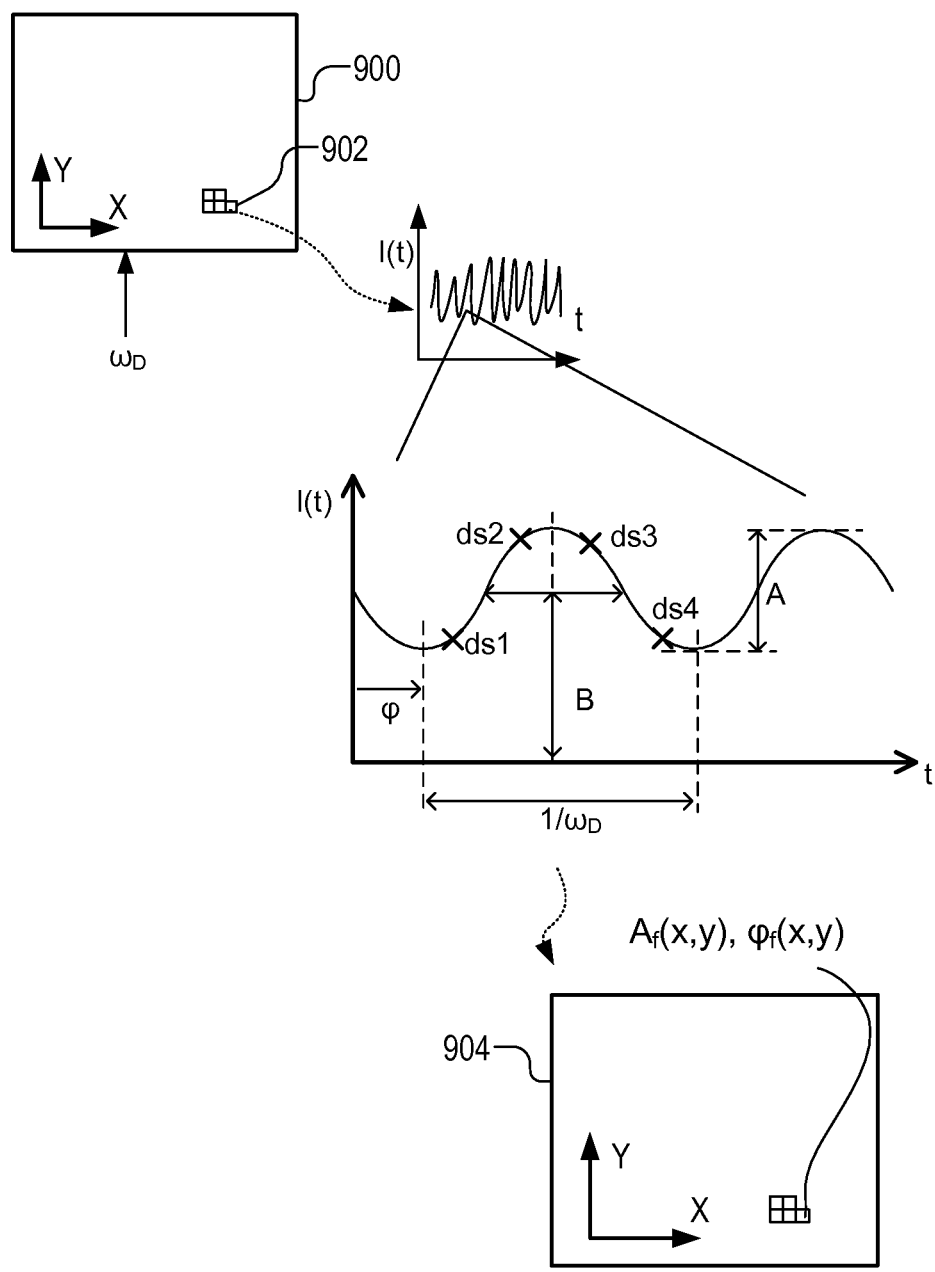
FIG. 10 illustrates the principle of operation of the lock-in image detector in the apparatus of FIG. 9.

FIG. 9 illustrates a modified focus monitoring arrangement 500', in which parts having the same function as in FIG. 5 have the same reference signs. The main difference between this arrangement and the one of FIG. 5 is that the detectors 520b, 520c (located in front of and behind a back the focal plane) are replaced by a single lock-in image detector 900, located in the back focal plane. FIG. 10 illustrates the principles of operation of lock-in image detector 900. A lock in image detector comprises an array of light-sensitive pixels 902, each locked at a detection frequency $\omega_D$. The axes of the array are labeled X and Y, with 902 representing a pixel at a position (x,y) of the sensor. Under control of processor PU, any of the shift frequencies $\Delta\omega_1, \Delta\omega_2 \ldots \Delta\omega_n$ from frequency source 555 can be selected as the detection frequency $\omega_D$.

The graph in FIG. 10 shows the temporal evolution of an illumination intensity I(t) incident on the detector 900 recorded at each pixel 902 (the signal is different at each pixel of course). A conventional image detector would simply integrate this intensity for an exposure interval, and output a single intensity per pixel. In the lock-in image detector, however, the radiation at each pixel is sampled separately multiple times (ds1, ds2, ds3, ds4) at intervals throughout a period of the reference frequency ($1/\omega_D$). For the present example, it is assumed that there are four sampling points per period, separated by 90°. Assuming that the intensity waveform I(t) contains a sinusoidal component synchronized with reference frequency $\omega_D$, this will give different values for the samples ds1-ds4 as illustrated. The samples ds1-ds4 may be integrated over several periods to obtain signals s1, s2, s3, s4. In this way, frequency components of the intensity waveform that are not synchronized with the reference frequency will be averaged out. The four values s1-s4 allow calculation of the phase and amplitude of the synchronized component. For example, the amplitude A, phase $\varphi$ and dc offset B of the synchronized component can be calculated by the formulae:

$$A = \frac{\sqrt{(s2-s4)^2 + (s1-s3)^2}}{2}$$

$$\varphi = \arctan\frac{(s1-s3)}{(s2-s4)}, \text{ and}$$

$$B = \sum_{i=1}^{4} s_i/4.$$

Intensity of this component can be calculated as $I=A^2$. These values can be calculated individually for each pixel 902.

In the application for focus monitoring, the phase images $\varphi(x,y)$ can be used to monitor focus without comparing two detector signals. Rather, a flat phase image ($\varphi$ constant across the image) will indicate an in-focus state. A non-flat phase image will indicate a defocus. The direction and magnitude of curvature of the phase front can be used by processor PU to calculate the direction and degree of defocus. The focus control signal FC can be generated accordingly.

The image sensor 132 may for example be an adapted CMOS image sensor. Note that single-photon avalanche diodes (SPADs), CCDs or any other suitable sensors may also be used as detectors. Readers skilled in the art will be able to adapt known lock-in methods and/or phase-sensitive detection methods to detect amplitude and phase images as described herein. While FIG. 3 shows the amplitude and phase values emerging from the lock-in image detector 112, it is a matter of design choice whether these values are calculated in the detector itself, or within the processing unit PU. In practice, it may be convenient if processing unit PU receives the raw samples ds1-ds4, or the integrated values s1-s4 from the lock-in image detector, and then performs the calculations of amplitude, phase, intensity as desired. Note also that amplitude and phase information need not be expressed in the form of values A and $\varphi$. The amplitude and phase information for each pixel may be represented by a pair of component vectors U and V. The conversion between these forms of expression is easily done by expressing the amplitude and phase as complex number according to the well-known relation:

$$U+iV=Ae^{i\varphi}$$

Compared with the embodiment of FIGS. 5 to 8, it may be noted that the lock-in image detector is unable to detect all frequencies simultaneously. With eight individual samples per pixel, two frequencies could be locked simultaneously in the same image detector, of two image detectors (with a beam splitter) could be provided. The arrangement would still not have the flexibility of processing the detected frequency spectrum digitally. Consequently, in such an embodiment, the lock-in frequency (and hence the optical wavelength) may be switched periodically to check for best signal quality, or the setting may be pre-defined in a metrology recipe. Similarly, when using the focus monitoring arrangement for controlling 'focus' in a system other than an inspection apparatus, the signal quality can be found by trying different frequencies, and/or by pre-defined selections based on knowledge of the target structure and/or prior tests.

On the other hand, the lock-in image detectors provide additional functionality that the simple detectors 520b, 520c may not. The amplitude and phase images captured by detector 900 can be used for a variety of purposes, not only focus control. The same image detector may be used for the actual inspection signals (501), as well as for focusing. The same image detector may be used for normalization signals (501), as well as for focusing. Normalization detector 520a may be a lock-in image detector with a different lock-in frequency.

Conclusion

The method and associated inspection apparatus disclosed herein enable one or more of the following benefits.

Accuracy of focus monitoring may be improved. Almost all uncorrelated noise sources follow a curve, which means measuring at a higher frequency (>10 kHz, for example) lowers the noise impact of such a noise source on the final measurement as we go to higher measurement frequency. By implementing this technique the impact of all random noise sources is significantly reduced.

A particular advantage is that the disclosed arrangement is robust against "dark" targets. Current focusing arrangements suffer deterioration in performance with substrates where the optical signal reflected back from the target is very low. Noise overwhelms the signal, creating a situation where noise frequencies disturb the focus measurement and rapid settling on a new target becomes impossible. By introducing the heterodyne principle and using two or more colors simultaneously, it becomes possible to make noise limited measurements of the focus signal even when the reflected light is sub-optimal due to resonant wavelength dependent scattering. Furthermore, signal to noise ratios can be improved by using a stronger reference signal (Local-Oscillator signal). In the example discussed above, this can be done by adjusting the attenuating device (ND filter wheel) to improve the signal to noise ratio in cases where the signal is low.

Although specific reference may be made in this disclosure to the use of focus monitoring and control arrangements in inspection apparatuses such as scatterometers, it should be understood that the disclosed arrangements may have application in other types of functional apparatuses, as mentioned already above.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A focus monitoring arrangement for an optical system, comprising:
a focus detection system, comprising one or more lock-in detectors, configured to:
receive collected focusing radiation after focusing radiation is reflected from a target;
receive reference radiation, the reference radiation configured to interfere with the collected focusing radiation in the focus detection system; and
determine whether the optical system is in focus with respect to the target,
wherein the reference radiation and the focusing radiation are provided with a relative frequency shift so that the interfering radiation detected in the focus detection system includes a time-varying component having a characteristic frequency corresponding to the relative frequency shift, and
wherein the one or more lock-in detectors are configured to operate with reference to the characteristic frequency.

2. The arrangement of claim 1, wherein:
the reference radiation and the focusing radiation are from a same source or sources as the focusing beam delivery system, and
the reference radiation does not interact with the target.

3. The arrangement of claim 1, wherein the focus detection system comprises:
a first lock-in detector of the one or more lock-in detectors configured to receive a first portion of the interfering radiation; and
a second lock-in detector of the one or more lock-in detectors configured to receive a second portion of the interfering radiation,
wherein the focus detection system is configured to determine whether the optical system is in focus by comparing the first portion of the interfering radiation detected by the first lock-in detector and the second portion of the interfering radiation detected by the second lock-in detector.

4. The arrangement of claim 3, wherein one of the first and second lock-in detectors is positioned in front of a conjugate of a front focal plane of the optical system and the other of the first and second lock-in detectors is positioned behind the conjugate of the front focal plane.

5. The arrangement of claim 4, wherein the focus detection system is configured to determine whether the optical system is in focus by comparing, directly or indirectly, a spatial extent of spots of radiation formed on the first and second lock-in detectors.

6. The arrangement of claim 1, wherein the focusing radiation and the reference radiation include radiation derived from one or more coherent radiation sources.

7. The arrangement of claim 1, wherein the focusing radiation and the reference radiation include radiation derived from one or more incoherent radiation sources.

8. The arrangement of claim 1, wherein:
the focusing radiation comprises first focusing radiation having a first wavelength range and second focusing radiation having a second wavelength range,
the reference radiation comprises first reference radiation having substantially the first wavelength range and second reference radiation having substantially the second wavelength range,
the first reference radiation and the first focusing radiation are provided with a first relative frequency shift and the second reference radiation and the second focusing radiation are provided with a second relative frequency shift so that the interfering radiation detected in the focus detection system includes a first time-varying component having a characteristic frequency corresponding to the first relative frequency shift and a second time-varying component having a characteristic frequency corresponding to the second relative frequency shift, and
the one or more lock-in detectors is configured to operate with reference to both the first and second characteristic frequencies and is operable to select which of the first and second focusing radiation is used to determine whether the optical system is in focus.

9. The arrangement of claim 8, wherein the first focusing radiation and the first reference radiation are derived from a first coherent radiation source and the second focusing radiation and the second reference radiation are derived from a second coherent radiation source.

10. The arrangement of claim 1, further comprising:
one or more adjustable attenuators for adjustably reducing intensity of the reference radiation.

11. The arrangement of claim 1, wherein the focus detection system is configured to generate a focus control signal for adjusting focus of the optical system on the target in response to the determination.

12. The arrangement of claim 11, wherein the focus detection system is configured to generate the focus control signal for adjusting a functional system to which the optical system of the focus monitoring arrangement is coupled.

13. The arrangement of claim 1, wherein the focus detection system is configured to use information of a phase, the time-varying component having characteristic frequency.

14. The arrangement of claim 13, wherein the focus detection system comprises a lock-in image detector.

15. The arrangement of claim 1, further comprising:
a frequency shifter in a path of the focusing radiation and configured to provide the relative frequency shift between the reference radiation and the focusing radiation.

16. The arrangement of claim 1, wherein the relative frequency shift is approximately 30 kHz or approximately 100 kHz.

17. The arrangement of claim 1, wherein the relative frequency is small relative to a frequency of the focusing radiation.

18. An inspection apparatus comprising:
a focus monitoring arrangement for an optical system, comprising:
a focus detection system, comprising one or more lock-in detectors, configured to:
receive first collected focusing radiation after first focusing radiation is reflected from a target, the first focusing radiation having a first wavelength range;
receive second collected focusing radiation after second focusing radiation is reflected from the target, the second focusing range having a second wavelength range;
receive first reference radiation, the first reference radiation having substantially the first wavelength range and configured to interfere with the first collected focusing radiation in the focus detection system;
receive second reference radiation, the second reference radiation having substantially the second wavelength range and configured to interfere with the second collected focusing radiation in the focus detection system; and
determine whether the optical system is in focus with respect to the target,
wherein the first reference radiation and the first focusing radiation are provided with a first relative frequency shift and the second reference radiation and the second focusing radiation are provided with a second relative frequency shift so that the interfering radiation detected in the focus detection system includes a first time-varying component having a characteristic frequency corresponding to the first relative frequency shift and a second time-varying component having a characteristic frequency corresponding to the second relative frequency shift, and
wherein the one or more lock-in detectors are configured to operate with reference to at least one of the first and second characteristic frequencies.

19. The inspection apparatus of claim 18, wherein the optical system comprises a high numerical aperture objective lens.

20. The inspection apparatus of claim 18, further comprising:
a first radiation source configured to supply inspection radiation; and
a second radiation source or sources, distinct from the first radiation source, configured to supply at least one of the first and second focusing radiations.

21. The inspection apparatus of claim 20, wherein the inspection radiation comprises broadband radiation, the at least one of the first and second focusing radiations comprises narrowband radiation of one or more wavelength ranges.

22. The inspection apparatus of claim 18, wherein the inspection apparatus is configured to form a pupil image for performance of angle resolved scatterometry on the target.

23. The inspection apparatus of claim 18, wherein the inspection apparatus is configured to form a dark field image for performance of diffraction based asymmetry measurements on the target.

* * * * *